(12) United States Patent
Hart et al.

(10) Patent No.: US 8,105,285 B2
(45) Date of Patent: Jan. 31, 2012

(54) SURGICAL ACCESS APPARATUS AND METHOD

(75) Inventors: Charles C. Hart, Summerville, SC (US); John R. Brustad, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 530 days.

(21) Appl. No.: 11/062,022

(22) Filed: Feb. 18, 2005

(65) Prior Publication Data

US 2005/0159647 A1      Jul. 21, 2005

Related U.S. Application Data

(62) Division of application No. 10/346,846, filed on Jan. 17, 2003, now Pat. No. 6,887,194.

(51) Int. Cl.
  *A61M 5/178* (2006.01)

(52) U.S. Cl. .................................. 604/164.01

(58) Field of Classification Search ............. 604/164.01, 604/264, 272; 600/153, 129, 127, 114, 101
See application file for complete search history.

(56) References Cited

U.S. PATENT DOCUMENTS

| | | | |
|---|---|---|---|
| 4,254,762 A | | 3/1981 | Yoon |
| 4,762,130 A | * | 8/1988 | Fogarty et al. ............. 606/159 |
| 5,334,150 A | | 8/1994 | Kaali |
| 5,407,427 A | | 4/1995 | Zhu et al. |
| 5,443,484 A | | 8/1995 | Kirsch et al. |
| 5,577,993 A | * | 11/1996 | Zhu et al. .................. 600/204 |
| 5,630,805 A | * | 5/1997 | Ternamian ................. 604/274 |
| 5,685,820 A | | 11/1997 | Riek et al. |
| 5,738,628 A | | 4/1998 | Sierocuk et al. |
| 5,842,971 A | | 12/1998 | Yoon |
| 5,941,852 A | * | 8/1999 | Dunlap et al. ........... 604/164.11 |
| 6,001,084 A | | 12/1999 | Riek et al. |
| 6,068,637 A | | 5/2000 | Popov et al. |
| 6,468,228 B1 | | 10/2002 | Topel et al. |

FOREIGN PATENT DOCUMENTS

WO      WO 96/01132      1/1996

OTHER PUBLICATIONS

European Patent Office, Supplementary Partial European Search Report for European Patent No. EP 04 70 1731 based on International Application No. PCT/US04/000695, dated Apr. 11, 2007. European Patent Office, Supplementary Partial European Search Report for European Patent Application No. EP 04 71 2378 and International Application No. PCT/US2004/004883, dated May 9, 2008.
Co-Pending U.S. Appl. No. 11/383,927, filed May 17, 2006. Title: Surgical Access Apparatus and Method.

* cited by examiner

*Primary Examiner* — Kevin C Sirmons
*Assistant Examiner* — Deanna K Hall
(74) *Attorney, Agent, or Firm* — John F. Heal; Patrick Y. Ikehara; Pui Tong Ho

(57) ABSTRACT

A laparoscopic insufflation device is provided in the configuration of a coil with a blunt tip. The device is capable of passing through the abdominal wall without cutting tissue, and exiting the abdominal wall substantially parallel to the inner surface. While rotation of the coiled device results in forward movement through the abdominal wall, a counter force can be applied to the device to create a safety space between the wall and the interior organs. With the blunt distal tip, parallel exit angle, and safety space, there is substantially no threat to the interior organs during placement of the device. Further space can be generated with the use of pressured gas to produce an abdominal cavity for the subsequent placement of trocars. By rotatably attaching the coiled insufflation device to a trocar, the advantage of a counter force can be used not only to establish the safety space but also to pull the trocar into the abdominal wall with a counterforce which resists tenting.

20 Claims, 15 Drawing Sheets

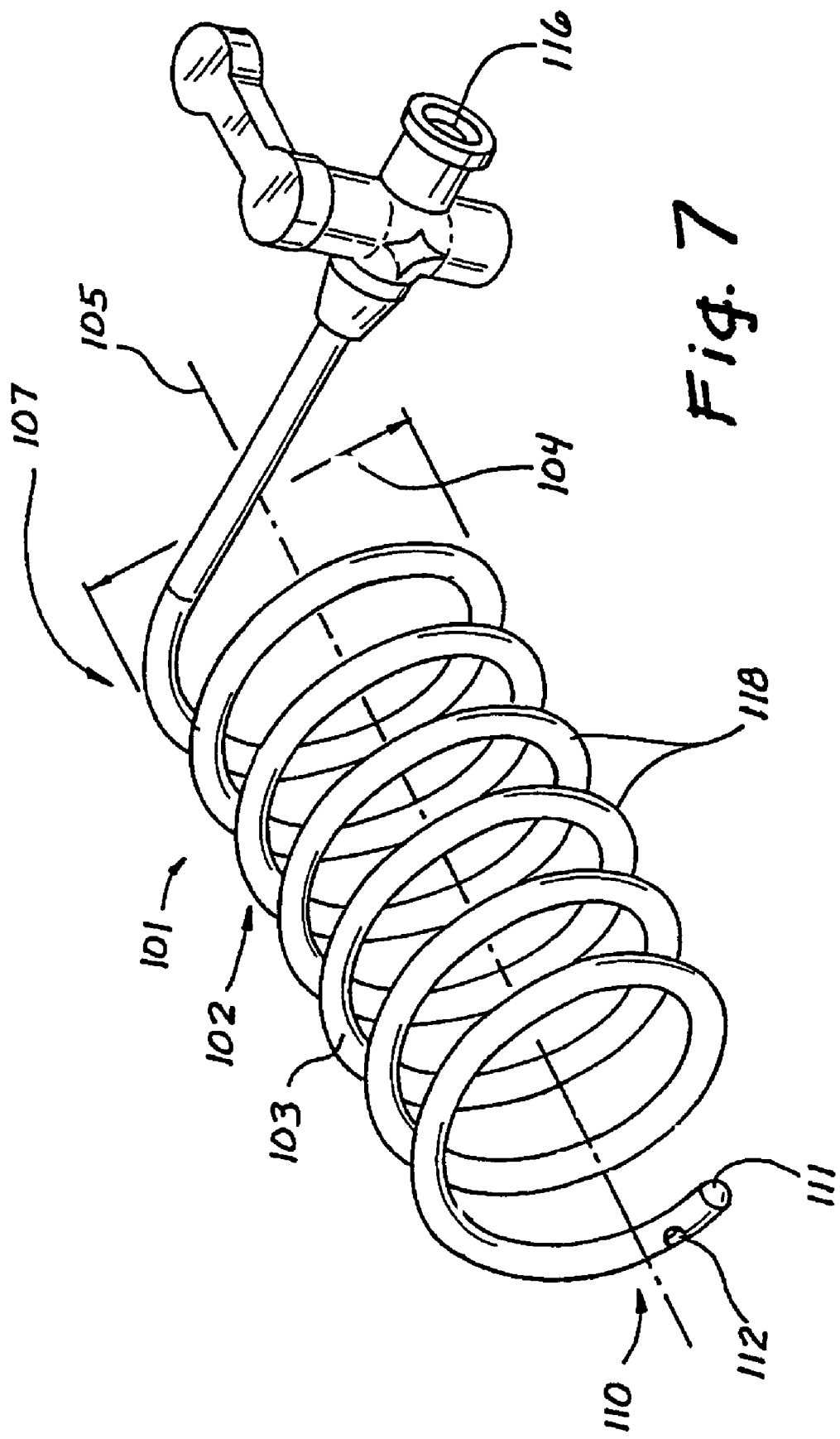

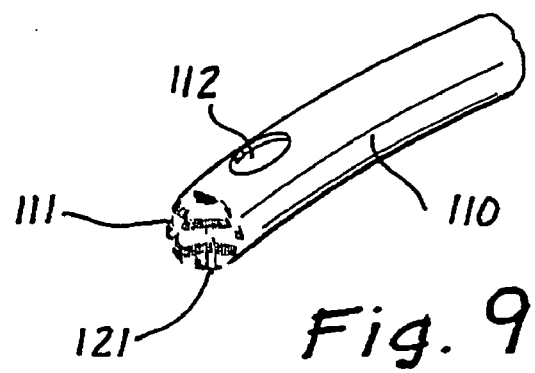
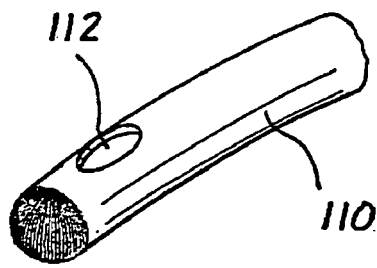
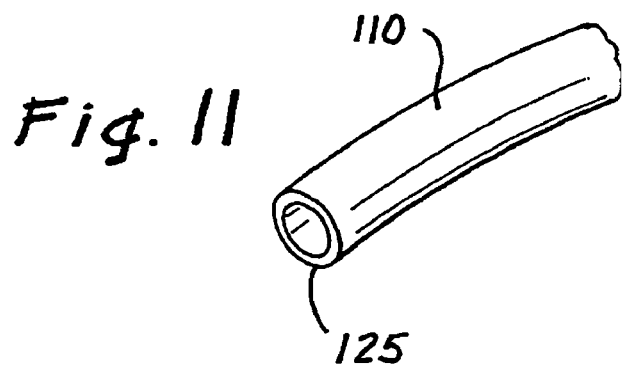
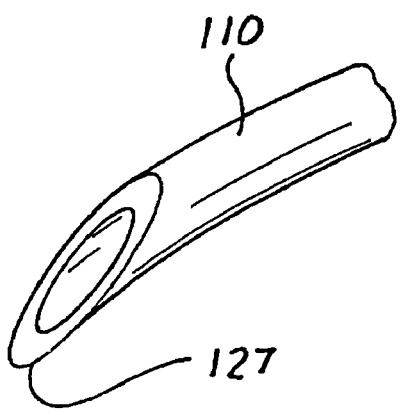

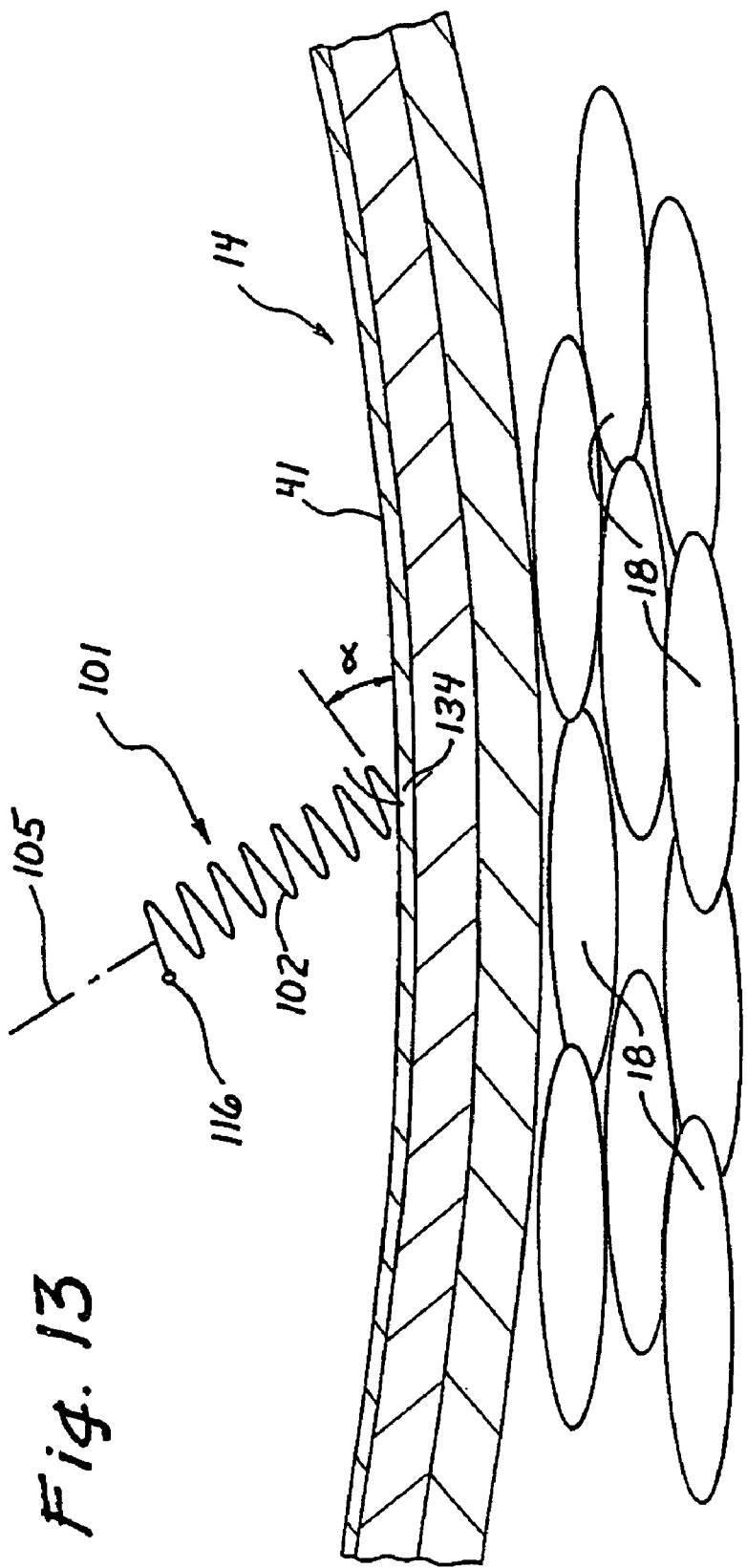

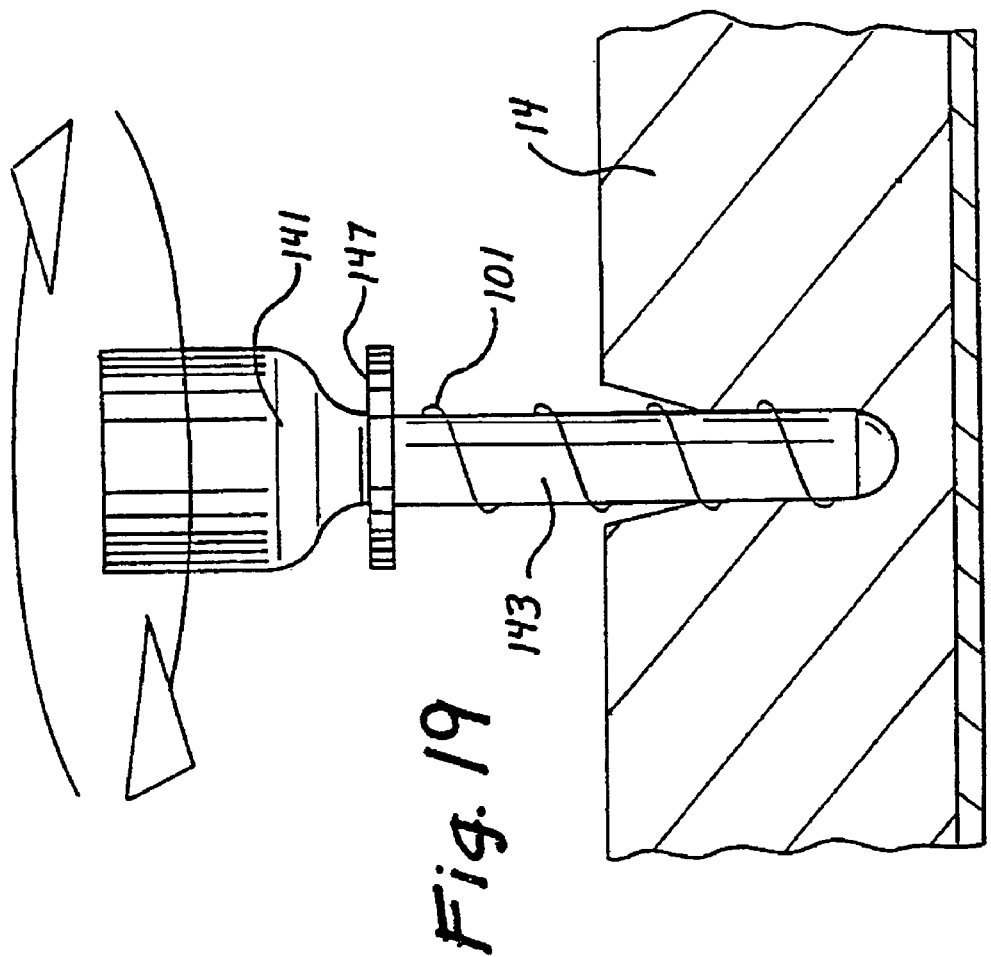
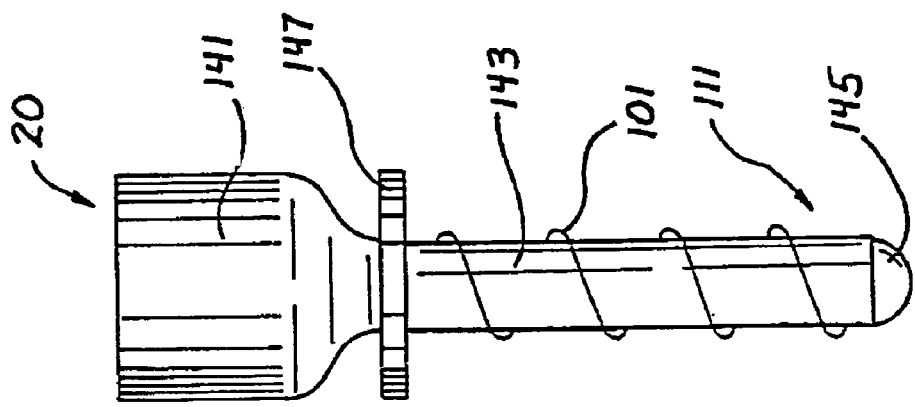

SURGICAL ACCESS APPARATUS AND METHOD

This is a divisional application of application Ser. No. 10/346,846, filed Jan. 17, 2003 now U.S. Pat. No. 6,887,194.

BACKGROUND OF THE INVENTION

1. Field of the Invention

This invention relates generally to surgical access devices and more specifically to trocars and insufflation devices used in laparoscopic surgery 2. Discussion of Related Art Abdominal inflation is a critical component of Laparoscopic Surgery. The most common method to achieve inflation, more commonly referred to as insufflation, is to pass a sharp needle through the abdominal wall and into the inner abdominal region, and then inject a gas through the needle and into the region thereby creating an enlarged or ballooned cavity to accommodate a laparoscopic procedure. Unfortunately, insertion of the needle has been required without any visual aid to facilitate location of the sharp needlepoint In order to reduce the probability of inadvertent penetration of delicate internal organs in this "blind" procedure, the sharp insufflation needle has been provided with a spring and retractable safety mechanism.

The safety mechanisms associated with most insufflation needles consist of a blunt or rounded member disposed within the lumen of the needle, and biased by a spring to an extended position beyond the needle tip This spring must be responsive to the insertion pressure during placement of the needle but must be capable of immediately moving forward when that pressure is relieved. This is highly mechanical event and at best, offers a less than optimal arrangement.

In order to make the insertion of sharp needles into the abdominal region safer, a common practice has developed where the needle is inserted at an angle to the tissue plane This of course requires that the needle traverse a greater distance through the abdominal tissue, so the maximum angle is always limited by the length of the needle.

Notwithstanding these attempts to reduce the probability and severity of an adverse consequence, many inadvertent injuries continue to result from the blind insertion of insufflation needles.

SUMMARY OF THE INVENTION

In a preferred embodiment of the present device, a length of hollow tubing, configured as a helix, is provided with a closed and rounded distal end At least one distal side opening allows insufflation gas to exit the spiral tube at the distal end. The proximal end of the spiral tube is fitted with a connecting hub and a valve for connection to a gas supply. In operation, the spiral tube is inserted into a small skin incision and subsequently rotated to separate or part abdominal tissue until the distal end emerges from the abdominal wall and into the abdominal region A significant characteristic of the spiral tube is that its distal tip emerges nearly parallel to the plane of the inner surface of the abdominal wall and the adjacent internal organs With this orientation, the blunt distal end of the device presents no danger to these delicate internal structures.

In one aspect, a laparoscopic insufflation needle is adapted for movement across an abdominal wall of a patient to insufflate an abdominal region of the patient, the needle comprises an elongate tube having an inflation channel extending between a proximal end and a distal end. The tube is adapted at the proximal end for connection to a source of fluid under pressure, and is adapted at its distal end to expel the fluid under pressure to insufflate the abdominal region of the patient. An optical element can be disposed at the distal end of the elongate tube to facilitate visualization of the abdominal wall and the abdominal region of the patient.

In another aspect, an insufflation needle is adapted for movement across an abdominal wall and into an abdominal region of a patient The needle includes an elongate tube for insufflating the abdominal region with a fluid under pressure. The tube is configured to provide a mechanical advantage when moved across the abdominal wall.

In another aspect, the insufflation needle includes an elongate tube for insufflating the abdominal region with a fluid under pressure The elongate tube at its distal end is angled relative to the proximal end of the tube to produce an exit angle with an interior surface of the abdominal wall This exit angle is in a range of less than about 40 degrees in order to inhibit penetration of interior organs of the patient.

In another aspect, the elongate tube of the insufflation needle has a distal end with a distal tip that is free of sharp edges to inhibit cutting the abdominal wall during penetration of the abdominal wall, and to inhibit cutting the interior organs following penetration of the abdominal wall.

An associated method for accessing an abdominal region of the patient by crossing an abdominal wail of the patient, includes the steps of providing an insufflation needle in the configuration of a tube, and turning the tube to facilitate the crossing of the abdominal wall with the insufflation needle.

In another method, an access device is used to create an abdominal cavity in an abdominal region containing interior organs of the patient. The method includes the steps of providing an elongate shaft having an axis extending between a proximal end and a distal end, and moving the shaft across the abdominal wall to place the distal end of the shaft in the abdominal region. Following this placement, the elongate shaft can be pulled to move the abdominal wall away from the interior organs and to create the abdominal cavity around the interior organs in the abdominal region.

In a further aspect, a surgical device is adapted to provide access across an abdominal wall and into an abdominal region of a patient The device includes a trocar having a cannula, and a shaft having a proximal end and a distal end The shaft has the configuration of a coil with a coil axis, the coil being adapted to facilitate rotational movement of the shaft across the abdominal wall shaft across the abdominal wail is accompanied by movement of the trocar into the abdominal wall.

In an associated method, a trocar is placed across an abdominal wall of a patient by providing a shaft in the form of a coil having a proximal end and a distal end. The proximal end of the coil is coupled to the trocar so that screwing the coil into the abdominal wall moves the trocar with the shaft into the abdominal wall with a mechanical advantage which is dependent upon the configuration of the coil.

In a further aspect, an anchor is adapted for use with a trocar having a cannula configured for placement in an operative position across an abdominal wall The anchor includes a structural element adapted to be coupled to the trocar and to extend outwardly of the cannula, the structural element having characteristics for engaging the abdominal wall at a location spaced from the cannula to inhibit withdrawal of the cannula from the operative position of the cannula.

DESCRIPTION OF THE DRAWINGS

FIG. 7 is a perspective view of one embodiment of the present insufflation device;

FIG. 8 is an enlarged perspective view of one embodiment of a distal end portion of the insufflation device illustrated in FIG. 7, FIG. 9 is an enlarged perspective view of the distal end portion of an alternate embodiment of the insufflation device;

FIG. 11 is an enlarged perspective view of the distal end portion in another embodiment of the insufflation device;

FIG. 12 is an enlarged perspective view of the distal end portion in a further embodiment of the insufflation device;

FIG. 13 is an enlarged cross-section view of the abdominal wall showing an initial step in a preferred method for insertion of the device;

FIG. 18 is a front elevation view of a combination including an insufflation device rotatably attached to a trocar; and FIG. 19 is a front elevation view showing the combination of FIG. 18 in use to cross the abdominal wall.

DESCRIPTION OF PREFERRED EMBODIMENTS AND BEST MODE OF THE INVENTION

Figure 1:
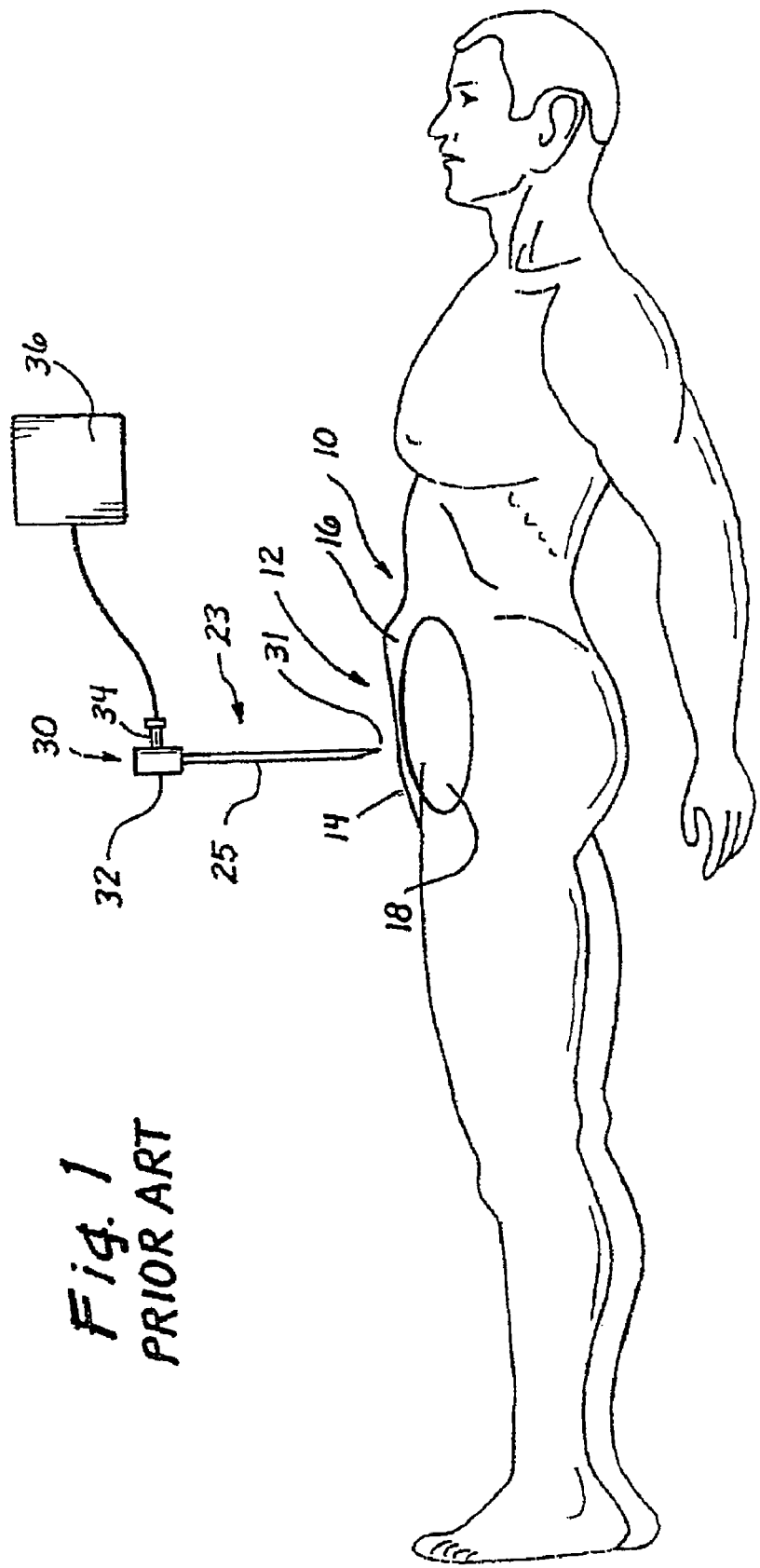
FIG. 1 is a side view of a patient in a prone position arid prepared for laparoscopic surgery.
Figure 2:
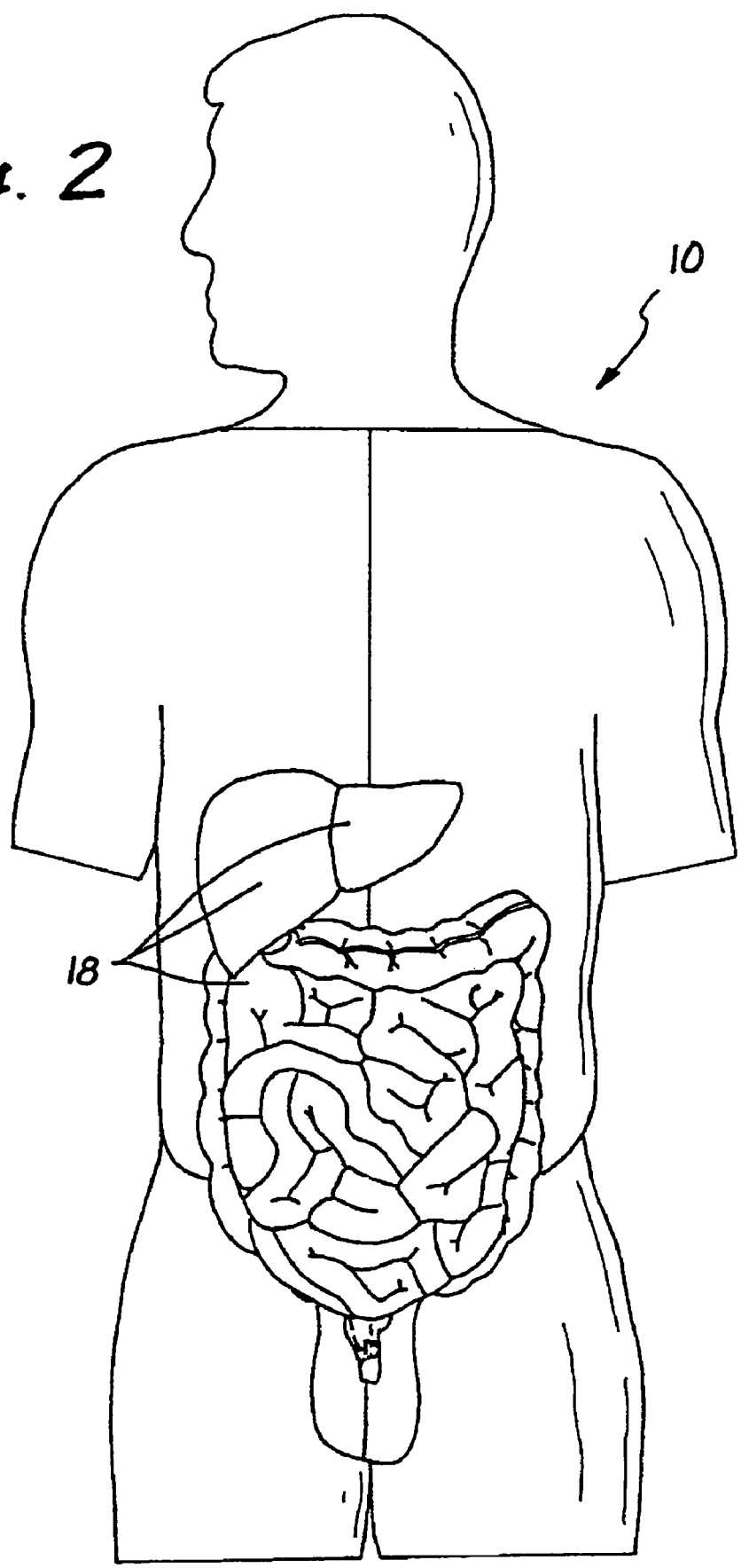
FIG. 2 is a top plan view showing organs internal to an abdominal region of the patient.

A patient is illustrated in FIG. 1 and designated generally by the reference numeral 10 The patient 10 is shown in a prone position with his abdomen 12 facing upwardly as he is readied for laparoscopic surgery In this process, minimally invasive surgery is undertaken through an abdominal wall 14 and within an abdominal region 16 of the patient. This Laparoscopic surgery commonly involves internal organs 18 as best illustrated in FIG. 2. Rather than accessing these internal organs 18 through a large opening in the abdominal wall 14, laparoscopic surgery calls for minimal invasion of the abdominal wall 14. through tubular access devices, commonly referred to as trocars These trocars are designated by the reference numeral 20 in FIG. 3.

The trocars 20 are placed through small openings in the abdominal wall to provide access for visualization and surgical instruments They are commonly provided with sharp points which although facilitating puncture of the abdominal wall, can be particularly threatening to the internal organs 18 which initially are in close proximity to the abdominal wall.

Figure 3:
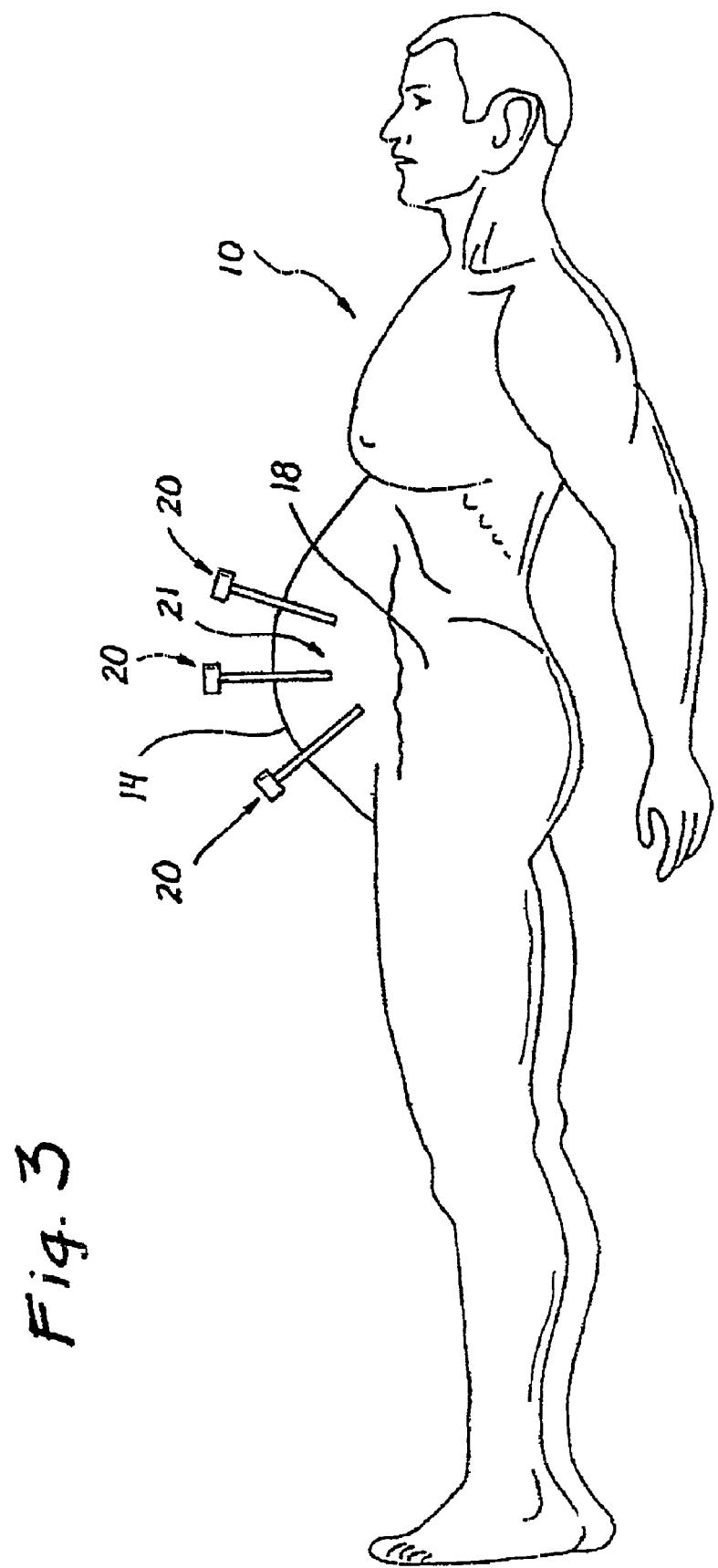
FIG. 3 is a side elevation view of the patient with an inflated abdominal cavity.

It is for this reason that placement of the trocars 20 is commonly preceded with inflation of the abdominal region in order to create an abdominal cavity 21. This initial step of inflating or insufflating the abdominal region 16 produces space between the abdominal wall 14 and the internal organs 18 as best illustrated in FIG. 3. With this separation or space, placement of the trocars 20 is facilitated with a reduced threat to the internal organs 18. Formation of the abdominal cavity 21 also increases the size of the operative environment and enhance visualization of the operative procedure Creation of the abdominal cavity 21 has typically been accomplished using an insufflation or Veress needle 23 as illustrated in FIG. 1. This needle 23 has included an elongate cannula 25 having a distal end 21 and a proximal end 30. At the distal end 27, the cannula has been provided with a sharp distal tip 31 of comparative interest to the present invention. At the proximal end 30, the cannula 25 has been coupled through a housing 32 to a connector 34 A source of gas under pressure 36 has been coupled to the.

Figure 4:
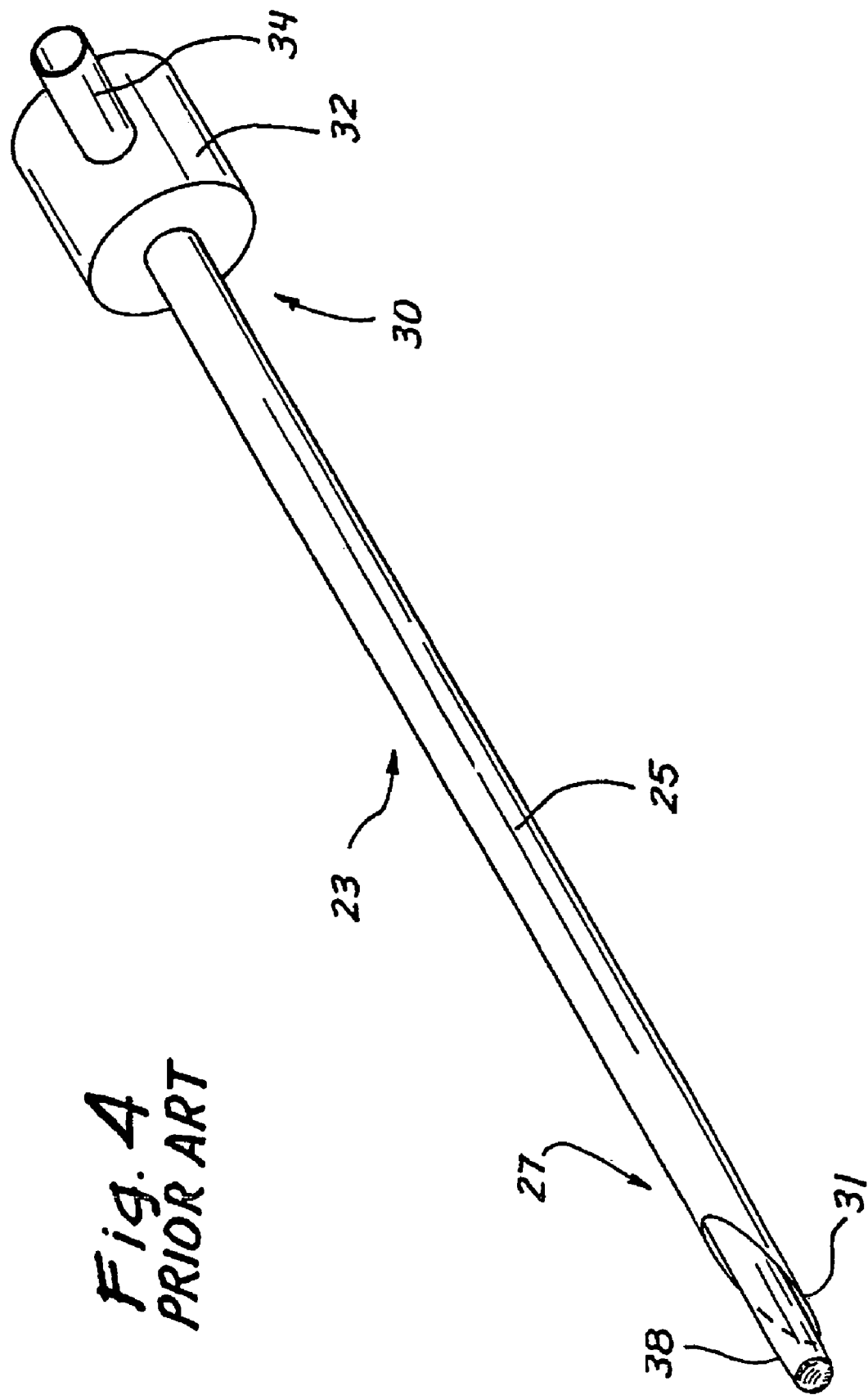
FIG. 4 is a perspective view of an insufflation needle of the prior art.

It is of particular importance to note that when the Veress needle 23 of the past is initially forced through the abdominal wall 14, there is no abdominal cavity 21. As a consequence, the internal organs 18 are not spaced from the abdominal wall 14, but are disposed closely adjacent to the abdominal wall 14 as illustrated in FIG. 1. In order to avoid puncture of these internal organs 18 by the sharp distal tip 31 of the insufflation needle 23, a spring actuated safety member 38 has been provided as best illustrated in the enlarged view of FIG. 4.

Note that the present procedure for placement of the Veress needle 10 has generally required that the needle be inserted perpendicular to the abdominal wall 14. This has produced a perpendicular exit angle with an inner surface 39 of the abdominal wall 14, and most importantly has produced a highly detrimental perpendicular relationship between the Veress needle 23 and the interior organs 18.

Figure 5:
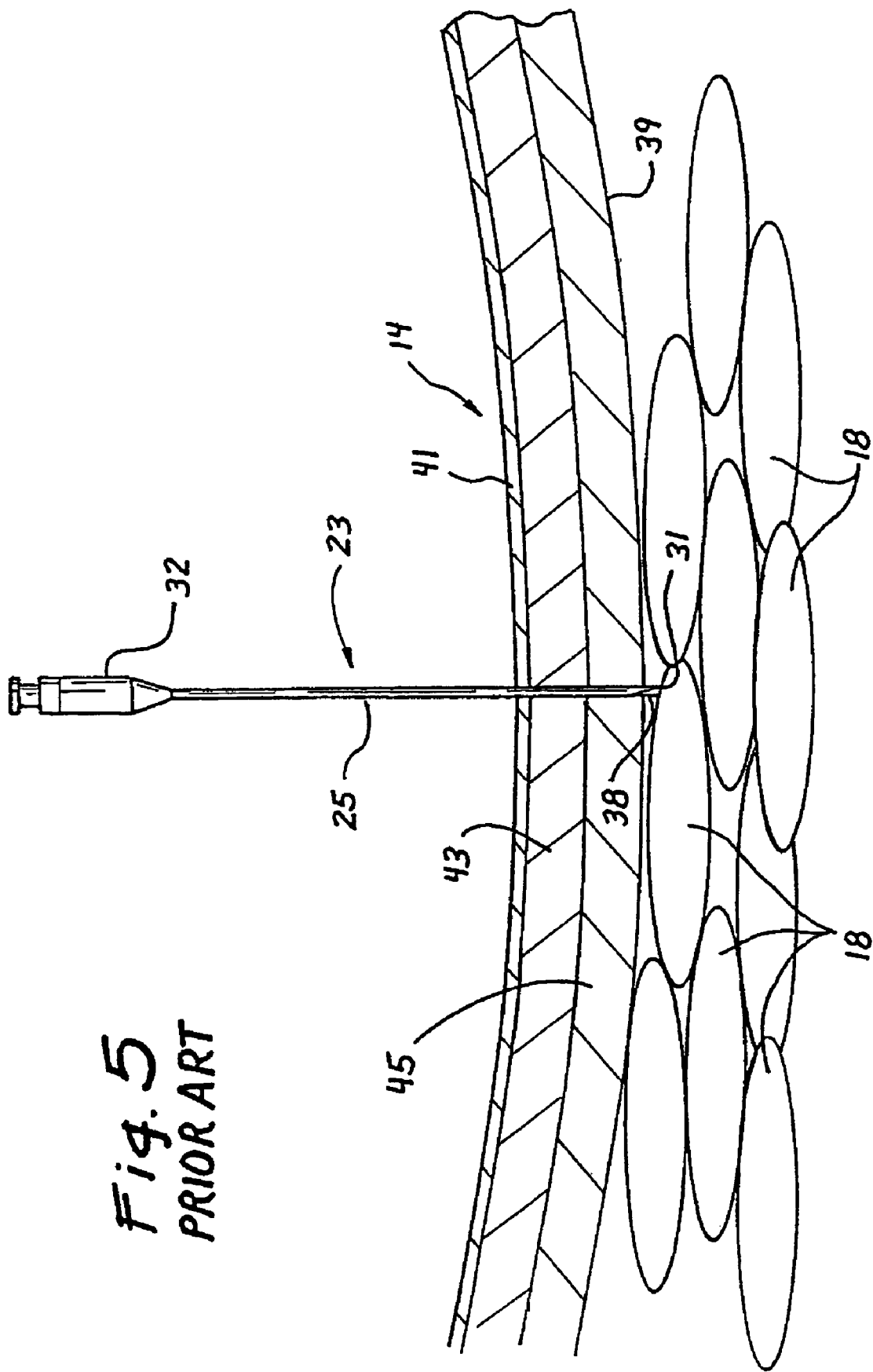
FIG. 5 illustrates an initial step in an insertion method associated with the insufflation needles of the prior art.

In order to fully understand this critical moment when an access device first emerges from the abdominal walls, reference is now made to FIG. 5 which shows a greatly enlarged view of the abdominal wall 14 with the internal organs 18 in close proximity. At the particular time illustrated, the Veress needle 23 has been forced through the abdominal wall 14 and the sharp distal tip 31 has Just become exposed at an inner surface 39 of the abdominal wall 14. With the intent of avoiding any damage to the internal organs 18 by the sharp distal tip 31, the safety member 38 has been deployed in this limited time and narrow space to shield the distal tip 31.

The mechanical requirements of this safety member deployment have limited the timeliness of this protection with consequent damage to the internal organs 18. While the safety member 38 reduces the probability of organ damage, the severity of this adverse occurrence remains significant. Furthermore, if a blood vessel is cut or an organ penetrated, the insufflation gas pressure will tend to inhibit any leakage that might alert one to the damage. Under these circumstances, the procedure can be fully completed with the resulting damage becoming apparent only after the insufflation pressure has been relieved and the operative site has been closed. This threatened exposure of the interior organs 18 can also be seen in the wider view of FIG. 6.

Figure 6:
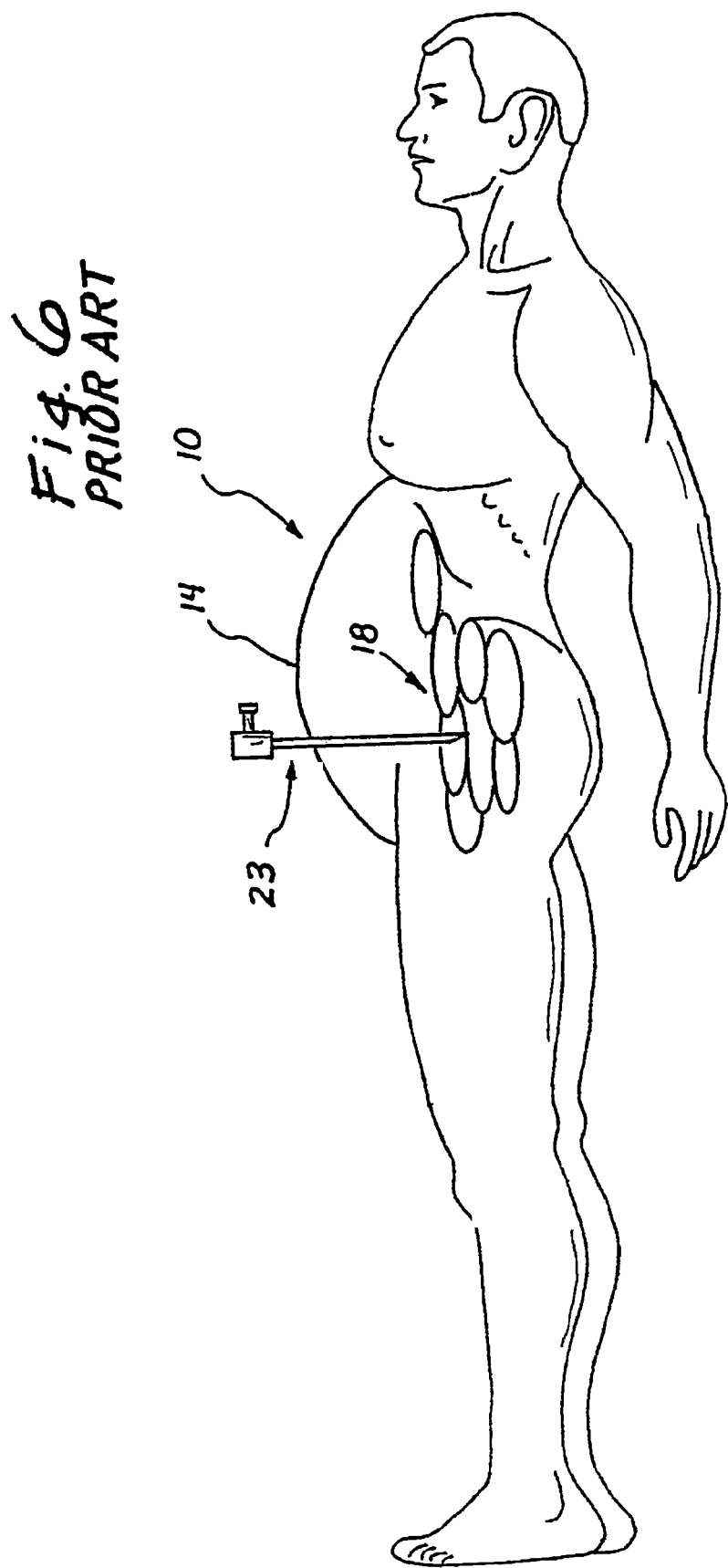
FIG. 6 illustrates an undesirable puncture of internal organs which can result when using the insufflation needles of the prior art.

It can be seen from FIGS. 5 and 6 that great care has been required during insertion of the Veress needle 23 in order to avoid damage to the adjacent internal organs 18. The needle 23 is commonly inserted through the abdominal wall 14 by pushing forward or distally The forward motion must be carefully controlled to avoid overshooting the abdominal wall 14 and inadvertently penetrating one of the internal organs 18 before the safety member 38 can respond and move forward to shield the sharp tip 31. This has required that the spring force be carefully balanced between that which is required to penetrate the abdominal wall 14 and that which is required to prevent penetration of the internal organs 18.

As illustrated in FIG. 5, the abdominal wall 14 consists of skin 41, layers of muscle 43 and a layer of connective tissue 45. In addition, there is a final, internal membrane 47 referred to as the peritineum This membrane 47, which forms the inner surface 39 of the abdominal wall 14, may be very thin and delicate or it may be very tough. In the latter case, the safety member 38 associated with the distal end 27 of the Veress needle 23 may be unable to respond in sufficient time to be effective, particularly if the peritineum exerts an elastic load as the needle 23 is urged forward. In short, an abrupt rupture of the peritineum 47 may allow a sharp, unshielded tip to penetrate the internal organs 18 before the safety member 38 can respond.

Referring to FIG. 7, a preferred embodiment of an insufflation device 101 of the present invention is shown in the configuration of a coil 102 formed of a spiraled length of hollow tubing 103. The coil 103 has a diameter 104, and an axis 105 extending between a proximal end 107 and a distal end 110.

At the distal end 110, a distal tip 111 can be rounded or blunted to ensure that there are no sharp edges to cut or tear body tissue The distal end 110 may have at least one side port 112 that permits gas to escape from the lumen of the tubing 103. The proximal end 107 of the coil 102 may include a tubular extension 114 terminating in a connector 116 which is adapted to be coupled to the source of gas 36 (FIG. 1). The coil 102 can be formed with individual convolutions 118 which are spaced to provide maximum engagement with the body tissue while avoiding overcompression and necrosis of the tissue.

With reference to FIG. 8, it will be appreciated that the distal end 110 of the coiled insufflation device 101 can be substantially or completely closed and formed with a hemispherical distal tip 111 providing a smooth transition to the coiled tubing 103. The side port 112 is preferably sized and configured to deliver maximum gas flow from the coiled tubing 103 to the abdominal cavity 21.

In an alternate embodiment illustrated in FIG. 9, the distal tip 111 is formed from a material that is optically clear. This allows use of an optical viewing device 121, such as an endoscope, angioscope or the like. In such an embodiment, the optical viewing device 121 could be disposed in the lumen of the coiled tubing 103 and subsequently advanced to the distal end 110 for visually monitoring insertion of the insufflation device 101.

It will be noted by comparison, that in the past, insertion of the Veress 10 needle 23 was a blind procedure which presented the greatest threat to the internal organs 18 (FIG. 2). Only after the Veress needle 23 had created the inflated abdominal cavity 21 and the first trocar 20 was placed, could an endoscope be inserted to facilitate visualization during insertion of subsequent trocars. With the present device, this visualization is available to provide for safe placement of the access device which initially crosses the abdominal wall 14.

Figure 10:
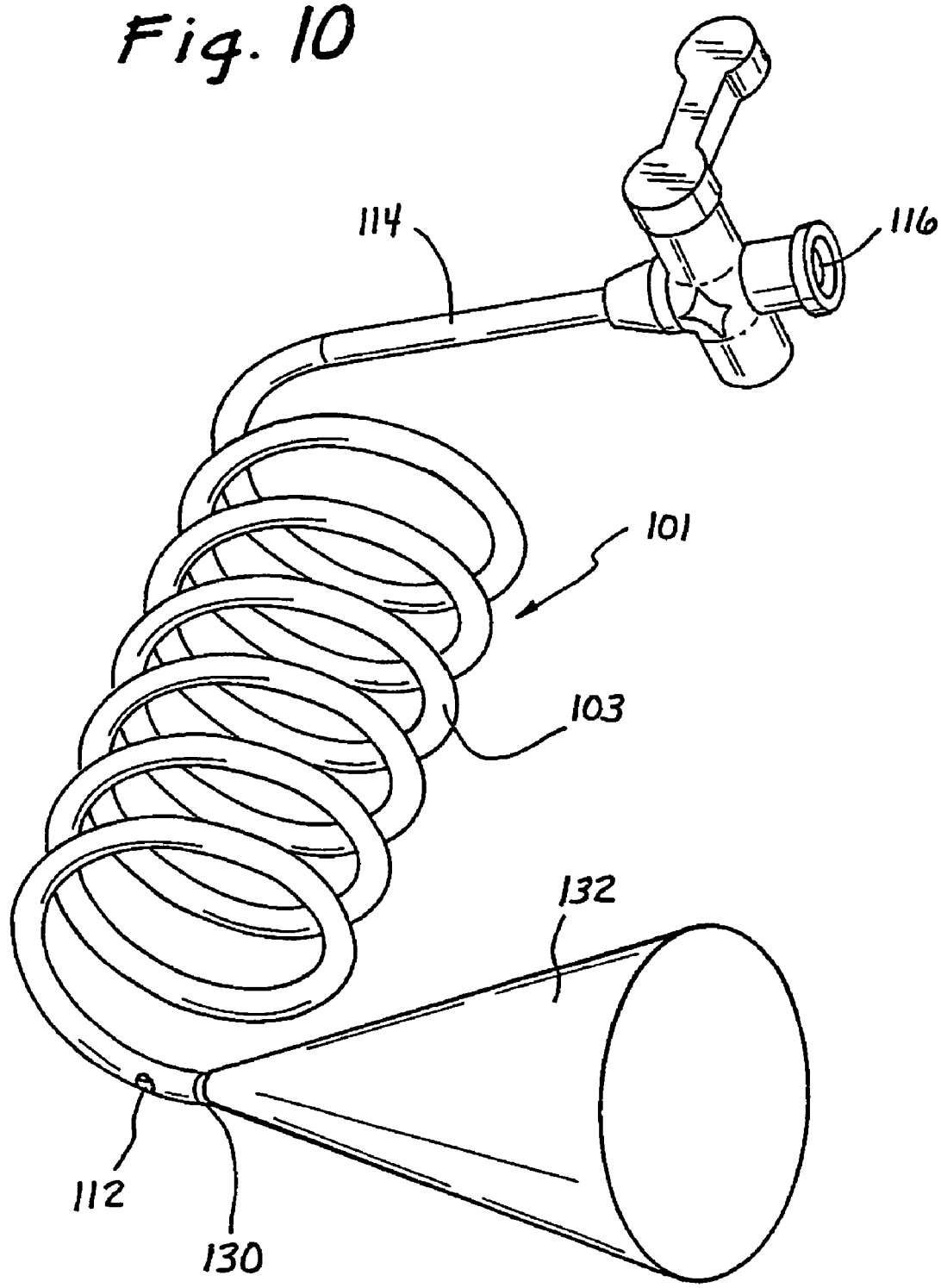
FIG. 10 is a perspective view of an alternate embodiment of the device including a distal tip emitting visible light.

In another embodiment illustrated in FIG. 10, the optical viewing device 121 may include an illumination device or light 130 within the lumen of the coiled tubing 103. In this case, the light 130 will produce an illuminated area 132 that is viewable from outside the body of the patient 10. This form of viewing, which is commonly referred to as transillumination, provides a clear indication as to the position of the distal end 110 when it has reached a preferred location The indication may be some change in the emission characteristics of the light 130, or may result from diffusion of the omitted light in a manner that indicates proper placement.

Referring now to FIGS. 11 and 12, the distal tip 111 of the coiled tubing 103 may present an end condition that is not rounded. For instance, the 5 coil tubing 103 may terminate in a straight perpendicular surface 125 as illustrated in FIG. 11. In this case, the lumen of the tubing 103 would be unobstructed.

In the embodiment of FIG. 12, the distal end 110 is provided with a sharp, pointed tip 127. Although the preferred embodiment of the present invention comprises a blunt or rounded tip 111, the sharp tip 127 of the FIG. 12 embodiment still offers the significant advantage associated with the reduced entry and exit angles provided by the coil construction.

Figure 14:
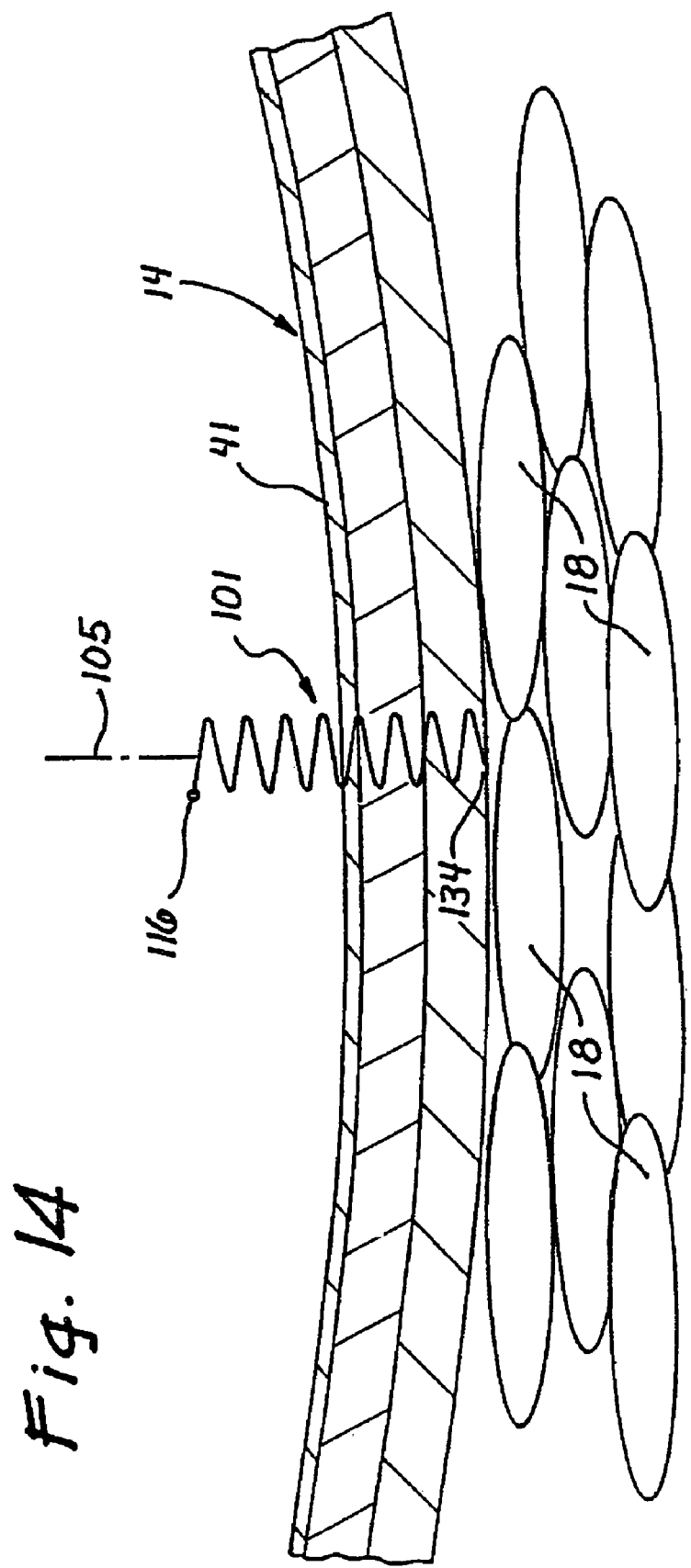
FIG. 14 is an enlarged cross-sectional view of the abdominal wall showing a continuing step in a preferred method for insertion.
Figure 15:
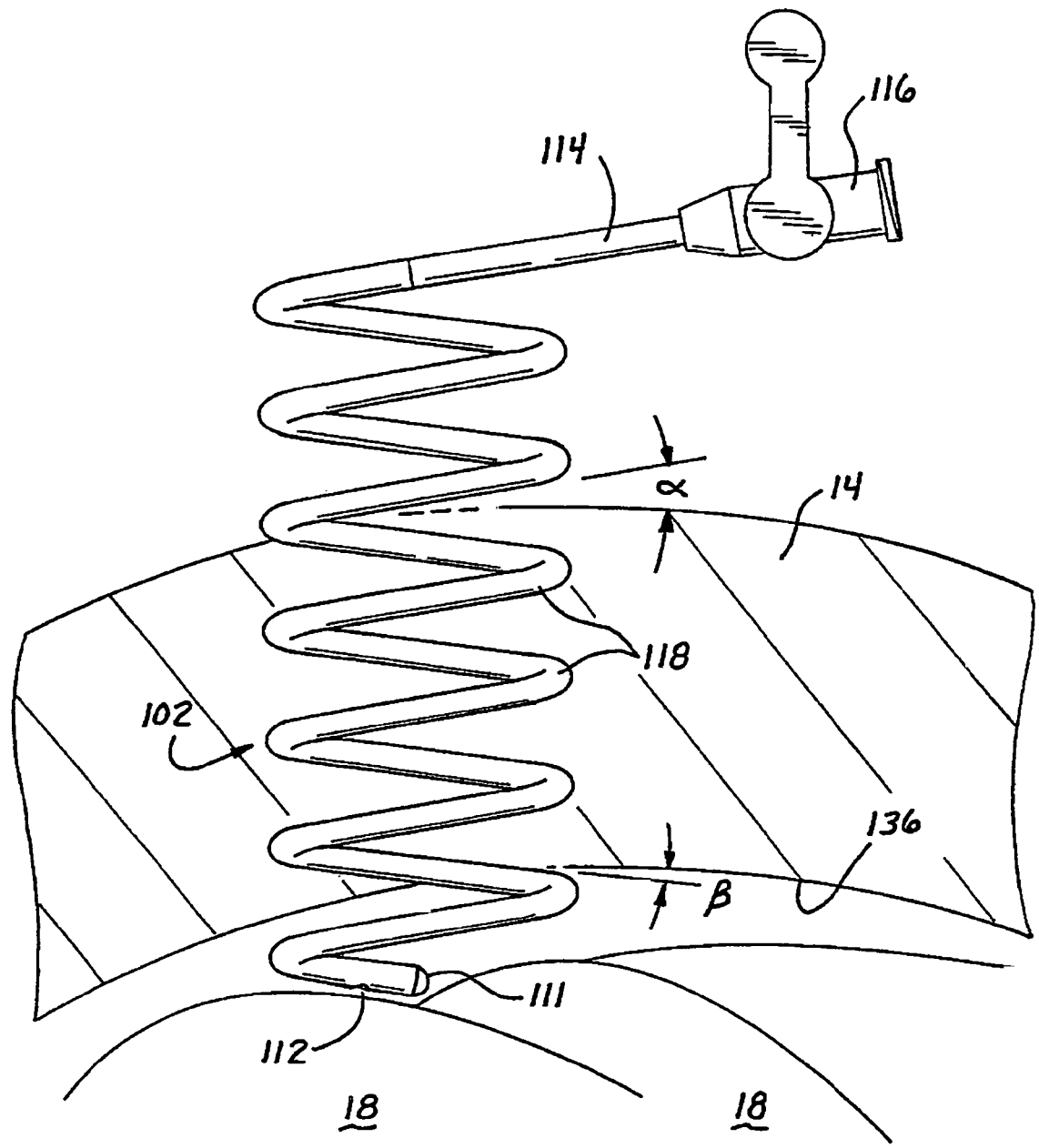
FIG. 15 is a close-up view of the abdominal wall illustrating a further step in the insertion method as the distal end emerges in close proximity to the internal organs of the patient.

These entry and exit angles can be further appreciated with reference to FIGS. 13, 14, and 15 which show progressive positions of the insufflation device 101 as it is maneuvered through the abdominal wall 14. In FIG. 13, a nick 134 has been made in the skin 41 of the wall 14. By placing the axis 105 of the coil 102 at an angle to the abdominal wall 14, the entry angle of the distal tip 121 can be increased to facilitate passage through the nick 134 In FIG. 13, this entry angle is designated by the Greek letter a. After the nick 134 has been penetrated, the coil 102 is preferably oriented so that its axis 105 is substantially perpendicular to the abdominal wall 14 as illustrated in FIG. 14. This greatly reduces the entry angle $\alpha$ as the distal tip 121 passes through the layer of muscle 43 and associated connective tissue 45 (FIG. 5) which comprise the abdominal wall 14.

Continued penetration of the coiled tubing 103 through the abdominal wall 14 is illustrated in FIG. 14. As the coil 102 passes through the abdominal wall 14, as illustrated in the enlarged view of FIG. 15, the distal tip and the following convolutions 118 exit the wall 14 at an exit angle designated by the Greek letter $\beta$ in FIG. 15.

It is this exit angle $\beta$ which is of particular importance to the present invention. Although this angle is measured with respect to an inner surface 136 of the abdominal wall 14, it can be appreciated that the internal organs 18 are also in contact with, or generally parallel to this inner surface 136. Accordingly, the exit angle $\beta$ is also the angle which the distal tip 121 presents to the internal organs 18. When this angle is generally perpendicular, as in the past (see FIG. 6), the probability of organ penetration is great. However, when this exit angle $\beta$ is reduced to a very small acute angle, the distal tip 111 tends to slide along the surface of the internal organs 18, particularly if the distal tip 111 has a blunt configuration as first discussed with reference to FIG. 8.

Figure 16:
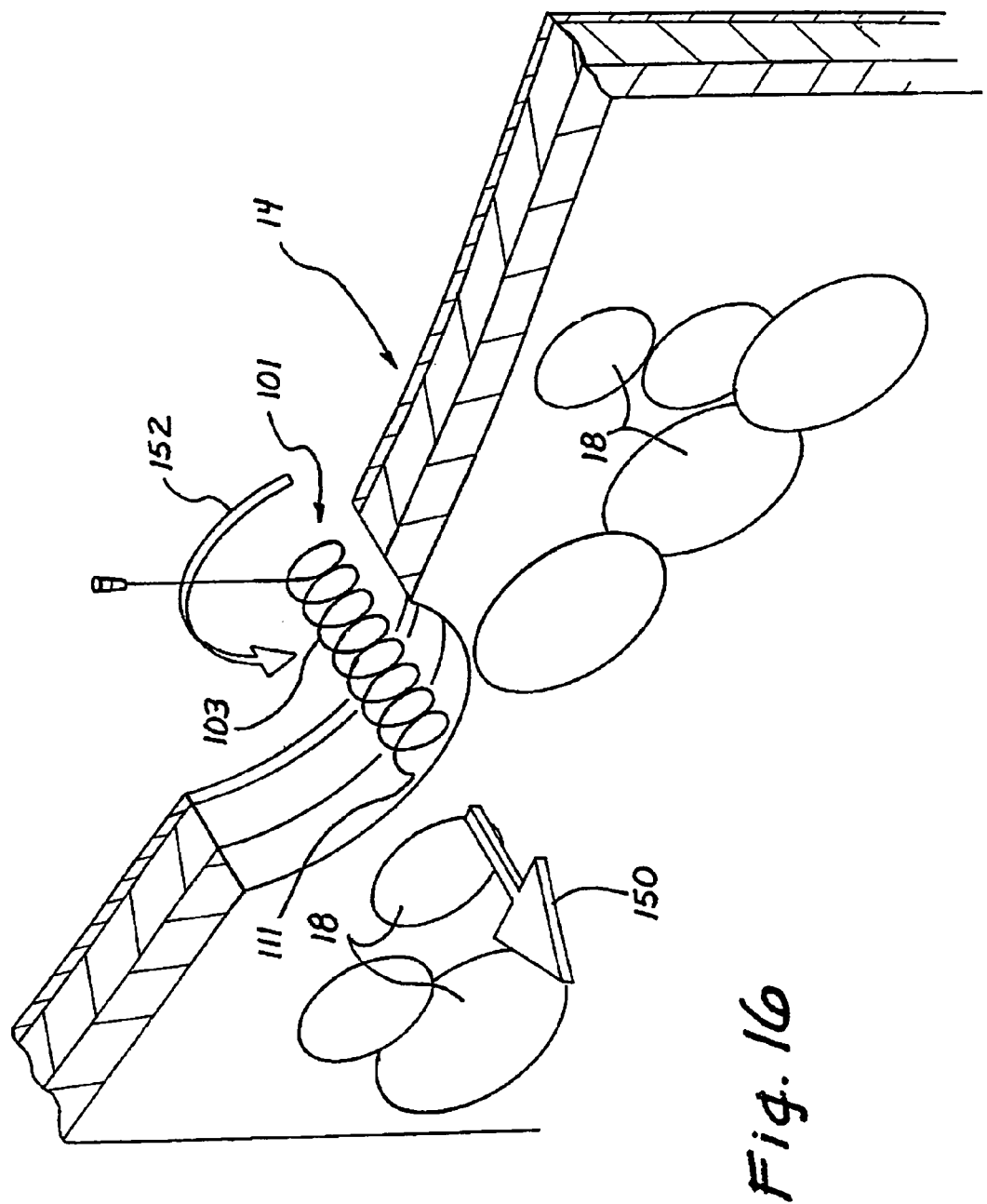
FIG. 16 is a schematic perspective view of the device within the abdominal wall.

In FIG. 16, the coiled device 101 of the present invention is illustrated schematically so that one can appreciate the forces associated with placement of the device 101 through the body wall 14. In the past, the straight Veress needle 23 (FIG. 1) would be placed using a force applied in the same direction as that desired for movement of the device 101, specifically a forward force applied in the direction represented by an arrow 150. Note that the insufflation device 101 of the present embodiment moves in the desired forward direction 150, but does so only in response to a rotational force represented by an arrow 152. The forward direction of movement illustrated by the arrow 150, may even be realized while the coiled tubing 103 is pulled backwardly by a force opposite to the forward direction of arrow 150. In other words, once the distal tip 111 is adequately engaged within the abdominal wall 14, FIG. 13, preferably within a small skin incision or nick 134 (FIG. 13), the entire device 101 may be held in traction rather than pushed to provide the desired forward motion. The coiled tubing 103 acts as a "corkscrew" and propels or advances itself in the forward direction 150, but only in response to rotational motion shown by arrow 152. This tractional rotation of the coiled tubing 103 tends to provide a safety margin as the body wall 14 is pulled or drawn away from the internal organs 18.

With further reference to FIG. 7, it can be seen that the present invention may comprise larger than ordinary tubing 103 since the placement force is not perpendicular to the abdominal wall 14 and internal organs 18. In fact, the placement force, as shown by arrow 152, is rotational arid incremental rather than direct and uncontrollable. In addition, the slow and deliberate advancement of the blunt distal end 110 gradually parts tissue, such as the skin 41, muscle 43, and connective tissue 45 in a more natural manner than with the straight, cuffing penetration of the past The blunt distal end 110 tends to wind its way through body tissue seeking weak, less dense or fatty tissue, and avoiding included blood vessels, and muscle that is normally more vascular than fatty tissue.

Figure 17:
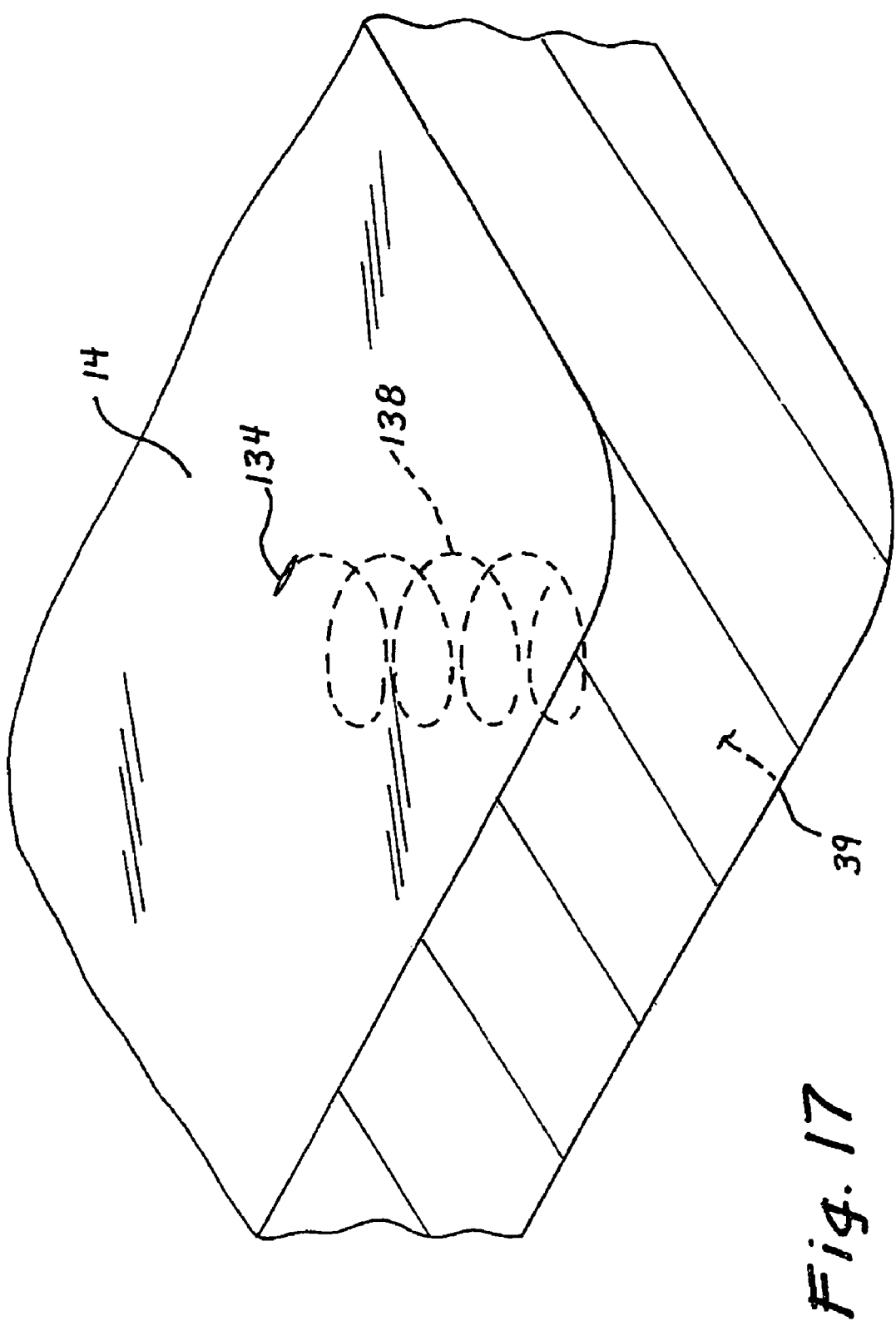
FIG. 17 is a perspective view of a wound site after removal of the device.

An insertion site 21 associated with the present invention is shown in FIG. 17 at a time when the device 101 has been removed, and the tissue, previously separated by the procedure, has generally returned to its original condition. Since little or no cutting has occurred, there is minimal bleeding and no potential for herniation of the site. A track 154 through which the device 101 passes as it is rotated through the tissue, has the same length and convoluted nature as the device 101 itself. With respect to the track 138, its length, convoluted nature and general lack of cut tissue provides improved healing even though the diameter size of the insufflation device 101 may have been as much as two or three times that of existing insufflation needles.

With further reference to this enlarged diameter, it will be noted that the insufflation device 101 can provide a gas flow significantly greater than existing insufflation needles. But even if the diameter or gauge size of the present insufflation device 101 is the same as that of the prior art, its gas flow will be significantly greater primarily due to the lack of obstruction in the lumen of the tubing 103.

Many of the advantages associated with the coiled insufflation device 101 can be further appreciated in combination with a trocar, such as the trocar 20 discussed with reference to FIG. 3. In this combination, illustrated in FIG. 18, the trocar 20 is shown to have a valve housing 141, a cannula 143, and a removable obturator 145. The coiled insufflation device 101 is rotatably attached to the trocar 20, for example with an attachment ring 147.

The trocar 20 is preferably disposed inside of and coaxial with the coiled insufflation device 101. With this orientation, the device 101 is free to rotate On its axis around the cannula 143 of the trocar 20. The device 101 will typically be as long as, if not slightly longer than, the cannula 143 so that the distal tip 111 extends at least to the tip of the obturator 145.

Operation of this combination is illustrated in FIG. 19. As the coiled insufflation device 101 is rotated into the abdominal wall 14 of the patient, it advances in the manner previously discussed. Due to its attachment to the trocar 20, this advancement tends to pull the trocar into the abdominal wall 14. One major advantage associated with this combination is that the device 101 provides an outward counter force which resists any tendency of the abdominal wall 14 to tent inwardly due to the forward movement of the trocar 20.

This system would be particularly useful for bariatric patients which have a large quantity of abdominal wall fa. In these patients, it is common practice to introduce the trocar at a slight angle to the patient's abdominal wall 14 in order to maintain it in place Often a large amount of leverage must be applied against the trocar to overcome the bulk of abdominal wall fat. This in turn widens the trocar entry wound and makes slippage of the trocar more likely. With the combination of the trocar 20 and insufflation device 101, the surgeon will not have to fight the abdominal wall during insertion and will further benefit from the tremendous retention provided by the insufflation device 101.

A further advantage associated with this combination can be appreciated by noting that trocars are typically placed normal to the surface of the abdominal wall 14 and also normal to the peritoneum. In the past, when the trocar 20 was pushed inwardly, the abdominal wall tented inwardly after the muscular layer of the abdominal wall 14 was penetrated, this inward force was applied directly to the peritineum and tended to separate the peritineum from the remainder of the abdominal wall. With the present combination, the coiled insufflation device 101 engages the peritineum and holds it against the remainder of the abdominal wall as the trocar 20 is pulled inwardly. As a result, the peritineum does not dissect from the abdominal wall.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of pads as well as their interaction. For these reasons, the above description should not be construed as limiting the invention, but should be interpreted as merely exemplary of preferred embodiments Those skilled in the art will envision other modifications within the scope and spirit of the present invention as defined by the following claims.

The invention claim is:

1. A surgical device adapted to provide access across an abdominal wall and into an abdominal region of a patient, comprising:
    a trocar including a cannula; and
    a shaft having a proximal end and a distal end; wherein
        the shaft comprising a coil with a coil axis, the coil facilitating rotational movement of the shaft across the abdominal wall;
        the proximal end of the shaft is fixedly axially coupled and freely rotatably coupled to the trocar about the coil axis so that movement by the shaft across the abdominal wall is accompanied by movement of the trocar into the abdominal wall;
        the distal end of the shaft terminates in a distal tip that is stationary relative to the shaft; and
        the distal tip of the shaft is blunt and free of sharp edges.

2. The surgical device recited in claim 1, wherein:
    the trocar has an axis; and
    the trocar axis is generally coincident with the coil axis.

3. The surgical device recited in claim 2, wherein:
    the trocar has a cannula with a distal tip forming a trocar exit angle with the abdominal wall;
    the shaft has a distal tip forming a shaft exit angle with the abdominal wall; and
    the trocar exit angle is greater than the shaft exit angle.

4. The surgical device recited in claim 3, wherein the distal tip of the cannula is generally perpendicular to the distal tip of the shaft.

5. The surgical device recited in claim 4, wherein the distal tip of the cannula is dimensioned and configured to be generally normal to the abdominal wall.

6. The surgical device recited in claim 1, wherein the shaft is dimensioned and configured such that a rotational movement of the shaft across the abdominal wall provides a mechanical advantage greater than unity to facilitate movement of the shaft across the abdominal wall, thereby providing provides a mechanical advantage greater than unity to facilitate movement of the trocar into the abdominal wall.

7. The surgical device recited in claim 1, further comprising a rotation ring carried by the trocar, wherein the proximal end of the shaft having a fixed relationship with the ring and a rotational relationship with the trocar.

8. The surgical device recited in claim 7, wherein the trocar has a cannula and the ring is rotationally supported by the cannula.

9. The surgical device recited in claim 7, wherein the distal tip of the cannula has a blunt configuration.

10. The surgical device recited in claim 1 wherein the shaft is hollow having a lumen extending from the proximal end to the distal end of the shaft.

11. The surgical device recited in claim 10 wherein the cannula of the trocar is hollow having lumen extending from a proximal end of the cannula to a distal end of the cannula.

12. The surgical device recited in claim 11 wherein the lumen of the cannula has a first diameter and the lumen of the shaft has a second diameter smaller than the first diameter.

13. The surgical device recited in claim 11 further comprising a trocar valve housing attached to the proximal end of the cannula and an obturator removable from and insertable into the lumen of the cannula through the distal end of the cannula.

14. The surgical device recited in claim 11, wherein
the lumen of the shaft has a diameter substantially smaller than a diameter of the lumen of the cannula, and
the diameter of the lumen of the shaft is dimensioned and configured to obstruct passage of an obturator through the lumen of the shaft and to allow passage of gas through the lumen of the shaft.

15. The surgical device recited in claim 10 further comprising a distal tip of the shaft dimensioned and configured to enclose the distal end and the lumen of the shaft.

16. The surgical device recited in claim 1 wherein the shaft extends along an entire length of the cannula to a distal end of the cannula.

17. The surgical device recited in claim 13 wherein the obturator has a proximal end and a distal end with a blunt hemispherical distal tip extending from the distal end of the obturator.

18. The surgical device recited in claim 3 wherein a fixed distance is maintained between the distal tip of the cannula and the distal tip of the shaft throughout operation of the device through the abdominal wall.

19. The surgical device recited in claim 15 wherein the shaft further comprises at least one side port on the distal end of the shaft.

20. The surgical device recited in claim 19, wherein the side port is fluidly coupled to the lumen of the shaft.

* * * * *